United States Patent [19]

Burgoyne, Jr. et al.

[11] Patent Number: 5,336,807
[45] Date of Patent: Aug. 9, 1994

[54] CROSSLINKING AGENTS FOR COATING AND ADHESIVE APPLICATIONS

[75] Inventors: William F. Burgoyne, Jr., Allentown; Jeremiah P. Casey, Emmaus, both of Pa.

[73] Assignee: Air Products & Chemicals, Inc., Allentown, Pa.

[21] Appl. No.: 77,580

[22] Filed: Jun. 15, 1993

[51] Int. Cl.$^5$ .............................................. C07C 49/00
[52] U.S. Cl. .................... 564/153; 564/158; 564/159; 568/587
[58] Field of Search .............. 568/587; 564/153, 158, 564/159

[56] References Cited

U.S. PATENT DOCUMENTS

| | | | |
|---|---|---|---|
| 4,663,410 | 5/1987 | Pinschmidt, Jr. et al. | 526/263 |
| 4,691,026 | 9/1987 | Pinschmidt, Jr. et al. | 548/531 |
| 4,788,288 | 11/1988 | Pinschmidt, Jr. et al. | 544/212 |
| 4,864,055 | 9/1989 | Pinschmidt, Jr. et al. | 560/160 |

OTHER PUBLICATIONS

CA67(13):62750m–Chemical Abstracts, "Phagocidal Action of Oxidized Spermine and Its Analogs," Fukami et al., 1967.

*Primary Examiner*—Bernard Lipman
*Attorney, Agent, or Firm*—Mark L. Rodgers; William F. Marsh

[57] ABSTRACT

Crosslinking agents are provided which are stable in both the solid state and in solution without undergoing uncontrolled self-crosslinking reactions. The crosslinking agents are formed by the amination of compounds having multiple ester moieties using homogeneous catalysis, and provide for formaldehyde-free crosslinking.

2 Claims, No Drawings

CROSSLINKING AGENTS FOR COATING AND ADHESIVE APPLICATIONS

TECHNICAL FIELD OF THE INVENTION

The present invention relates to alternatives to the use of formaldehyde-based crosslinking agents, e.g. melamine/formaldehyde, in coating and adhesive applications.

BACKGROUND OF THE INVENTION

Emulsion and solution polymers find wide application as adhesives, binders and coatings. Unfortunately, many of these polymeric materials, especially those prepared predominantly from vinyl acetate, ethylene, vinyl chloride, or their mixtures, show inadequate resistance to water and other solvents in their everyday use. In particular, they experience substantial and unacceptable loss in strength in the presence of solvents such as perchloroethylene, methyl ethyl ketone and toluene. In addition, many of these polymers exhibit deficiencies in adhesion to the substrates on which they are used, for example vinyl acetate, ethylene or vinyl chloride polymers on glass, metal or polyester. These deficiencies are reduced, especially for relatively hydrophilic monomers, by the use of adhesion promoting or crosslinking comonomers and/or post-added crosslinkers.

Among types of widely used crosslinking materials are aminoplasts, especially N-methylolacrylamide, melamine/formaldehyde and urea-formaldehyde condensates. These materials have met substantial success because they are low in cost, highly compatible with aqueous emulsion systems, rapidly cured under acid catalysis and are substrate reactive in that, for example, they react with the hydroxyl groups of cellulosic materials. These crosslinking materials, however, suffer from two deficiencies: (1) the emission of low levels of formaldehyde during cure and subsequent use, and (2) inadequate adhesion to certain substrates, for example, metal, glass and polyester.

Many attempts have been made to overcome or minimize the first deficiency, especially after the potential carcinogenicity and irritant properties of formaldehyde became widely recognized.

To reduce the level of formaldehyde in emulsion products, the use of O-alkylated N-methylolacrylamides such as butoxymethylacrylamide or the use of about equimolar ratios of N-methylolacrylamide with acrylamide were introduced. These materials did not, however, totally eliminate the presence of formaldehyde.

U.S. Pat. Nos. 4,691,026, 4,663,410, 4,788,288 and 4,864,055 disclose self- and hydroxyl reactive formaldehyde-free cyclic hemiamidal and hemiamide ketal monomers and polymers formed from such monomers. The monomers can be incorporated into free radical addition polymers which undergo efficient acid catalyzed, thermally activated post-crosslinking with themselves or, alternatively, can react with active hydrogen-containing comonomers of the polymers and/or with groups on the substrate to which the polymer is applied. These materials were advantageous over prior crosslinking systems in that they provided for good crosslinking and adhesion promotion without the accompanying emission of formaldehyde.

SUMMARY OF THE INVENTION

The present invention is a class of crosslinking agents which provide for formaldehyde-free crosslinking and are viable alternatives to the prior art melamine/formaldehyde based systems. These crosslinking agents are typically formed by the amination of compounds having multiple ester moieties using homogeneous catalysis. The resultant crosslinking agents have been found to be stable materials in the solid state, in the melt (<100° C.), and in solution without undergoing uncontrolled self-crosslinking reactions.

The present invention is also a curative coating system which comprises the crosslinking agent described above along with a polymeric material which contains active hydrogen, such as an acrylate resin or a polyester polyol resin.

DETAILED DESCRIPTION OF THE INVENTION

We have developed crosslinking agents which are stable in both the solid state and in solution without undergoing uncontrolled self-crosslinking reactions. Additionally, these crosslinking agents provide an alternative to prior art melamine/formaldehyde systems. The crosslinking agents can be formed by the amination of compounds having multiple ester moieties using homogeneous catalysis, and can be represented by the structural formula (I):

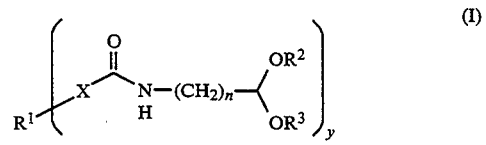

wherein $R^1$ is an aliphatic or aromatic multiradical; $R^2$ and $R^3$ are independently $C_1$–$C_6$ linear or branched alkyl, aryl or glycol, or $R^2$ and $R^3$ together form a $C_2$–$C_6$ alkylene group; X is a single bond, an oxygen atom, or NH; n is from 1 to 4; and y is an integer from 2 to 5.

Examples of suitable multi-ester compounds which can be aminated to form the above crosslinking agents include aliphatic, cycloaliphatic and aromatic (i) polycarboxylic acid esters, (ii) isocyanates and (iii) carbonyl chlorides. Preferred aminating agents include 4,4-dimethoxybutyl amine and 4,4-dimethoxypentyl amine. The catalysts used to carry out the amination reactions are organometallic catalysts such as titanium alkoxides or tins.

These multiple acetal containing crosslinking agents have been prepared in high yield, and by judicious choice of the ester substrate ($R^1$), the properties of the crosslinking agent can be tailored to meet the specific needs of a particular application. Specific examples of compounds which have been found to be useful crosslinking agents in adhesive and coating applications include N,N'-Bis(4,4-dimethoxybutyl)isophthalamide and N,N'-Bis(4,4-dimethoxybutyl)terephthalamide.

Typically, these crosslinking agents are employed as a component of a curative coating system which also comprises a polymeric material containing active hydrogen. Examples of suitable polymeric materials include polyester polyol resins and acrylate resins.

The following examples illustrate this invention and are not intended to limit its scope. Table 1 provides a summary of the novel compositions prepared and the scope of the catalyst types used in their preparation.

EXAMPLE 1

Preparation of N,N'-Bis(4,4-dimethoxybutyl)isophthalamide Using Dibutyl Tin Dimethoxide as Catalyst.

A 250.00 g (1.29 mol) portion of dimethyl isophthalate was dissolved in 2000 g of mixed xylenes contained in a 5 L, three-necked, round-bottomed flask fitted with a Dean-Stark trap, a thermometer, an addition funnel, and a mechanical stirrer. With rapid stirring, 25.00 g (0.0847 mol) of dibutyl tin dimethoxide was added followed by raising the temperature of the solution to 130° C. 4,4-Dimethoxybutylamine (372.9 g, 2.80 mol) was then added dropwise to xylene solution through the course of 30 min. The reaction temperature was maintained at 130° C. for 5 hr while collecting ca. 190 g of a methanol/xylenes (ca. 1:1) distillate. (After gas chomatographic analysis of the distillate, it was determined that greater than 90% of the theoretical amount of methanol had been isolated.) The Dean-Stark trap was removed and a Claisen distillation head was fitted to the flask. Approximately 750 g of mixed xylenes were removed via atmospheric distillation, then the remaining solution was filtered while hot. Upon cooling, a white precipitate formed which was collected and recrystallized twice from mixed xylenes. After vacuum oven drying (55°-60° C./1.0 mm Hg) the product overnight, an isolated yield of 425 g (1.07 mol, 83.0% yield) was realized; mp 74.5°–75.5° C.; IR (KBr) 1630 (C=O), 1595, 1560, 1130, 1045, 915, 705 cm$^{-1}$; $^1$H NMR (CDCl$_3$; 300 MHz) δ1.50–1.60 (m, 8H, —CH$_2$CH$_2$CH—), 3.22 (s, 12H, —OCH$_3$), 3.31 (m, 4H, NH$_2$CH$_2$—), 4.26 (t, 2H J=4.8 Hz, CH$_2$CH—) 7.12 (t, 2H, J=5.6 Hz, —NH—CH$_2$—), 7.33 (t, 1H, J=7.7 Hz, ArH), 7.80 (d, 2H, J=7.7 Hz, ArH) 8.09 (s, 1H, ArH); $^{13}$C NMR (CDCl$_3$; 75.5 MHz) δ23.9, 29.6, 39.4, 52.5, 103.8, 125.0, 128.1, 129.5, 134.4, 166.7; MS (70 eV) m/z (rel. intensity) 100 (84.56), 104 (100.00), 163 (78.68), 232 (44.67), 274 (26.47), 333 (17.10); HRMS (FAB) 419.2158 (M+Na).

EXAMPLE 2

Preparation of N,N'-Bis(4,4-dimethoxybutyl)isophthalamide Using Titanium Tetraisopropoxide as Catalyst.

Dimethyl isophthalate (50.00 g, 0.257 mol) was aminated with 74.59 g (0.560 mol) of 4,4-dimethoxybutylamine and 28.42 g (0.100 mol) of titanium isopropoxide in 400 g of mixed xylenes according to the procedure used in Example 1. A product mass of 69.38 g (0.175 mol, 68.1% isolated yield) was realized after recrystallization with mixed xylenes; mp 74° C.

EXAMPLE 3

Preparation of N,N'-Bis(4,4-dimethoxybutyl)terephthalamide Using Dibutyl Tin Dimethoxide as Catalyst.

Dimethyl terephthalate (25.00 g, 0.129 mol) was aminated with 37.29 g (0.280 mol) of 4,4-dimethoxybutylamine and 2.50 g (0.00847 mol) of dibutyl tin dimethoxide in 200 g of mixed xylenes according to the procedure used in Example 1. A product mass of 45.09 g (0.114 mol, 88.2% isolated yield) was realized after recrystallization with mixed xylenes; mp 129°–31° C.; IR (KBr) 1630 (C=O), 1545, 1135, 1055 cm$^{-1}$; $^1$H NMR (CDCl$_3$; 300 MHz) δ1.60–1.80 (m, 8H, —CH$_2$CH$_2$CH—), 3.31 (s, 12H, —OCH$_3$), 3.44 (m, 4H, —NH$_2$CH$_2$—), 4.37 (t, 2H, J=5.0 Hz, CH$_2$CH—), 6.71 (t, 2H, J=5.4 Hz, —NH—CH$_2$—), 7.74 (s, 4H, ArH); $^{13}$C NMR (CDCl$_3$; 75.5 MHz) δ24.0, 29.7, 39.5, 52.6, 104.0, 126.8, 136.8, 167.0; MS (70 eV) m/z (rel. intensity) 55 (100.00), 100 (55.17), 174 (19.83), 216 (54.31), 232 (44.83), 333 (13.15); HRMS (FAB) 419.2158 (M+N

EXAMPLE 4

Preparation of N, N', N'''-Tris(4,4-dimethoxybutyl)-1,3,5-benzenetricarboxamide.

Trimethyl 1,3,5-benzenetricarboxylate (25.00 g, 0.0991 mol) was aminated with 42.62 g (0.320 mol) of 4,4-dimethoxybutylamine and 3.00 g (0.0102 mol) of dibutyl tin dimethoxide in 200 g of mixed xylenes according to the procedure used in Example 1. This procedure afforded 50.53 g (0.0909 mol, 91.8% isolated yield) of the desired N, N', N'''-tris(4,4-dimethoxybutyl)-1,3,5-benzenetricarboxamide after recrystallization from mixed xylenes, mp 86°–88° C.; IR (KBr) 1635 (C=O), 1560, 1305, 1130, 1075, 1025 cm$^{-1}$; $^1$H NMR (CDCl$_3$; 300 MHz) δ1.60–1.70 (m, 12H, —CH$_2$CH$_2$CH—), 3.28 (s 18H, —OCH$_3$), 3.39 (m, 6H, —NH$_2$CH$_2$—), 4.33 (t, 3H, J=4.8 Hz, CH$_2$CH—), 7.17 (t, 3H, J=5.5 Hz, —NH—CH$_2$—), 8.27 (s, 3H, ArH); $^{13}$C NMR (CDCl$_3$; 75.5 MHz) δ25.2, 30.1, 40.4, 52.1, 104.2, 126.8, 136.8, 169.2; MS (70 eV) m/z (rel. intensity) 75 (100.00), 191 (8.33), 221 (8.87), 290 (5.94), 401 (2.58), 427 (2.28), 428 (2.84), 460 (4.61); HRMS (FAB) 578.3054 (M+Na).

EXAMPLE 5

Amination of Trimethyl 1,2,4-Benzenetricarboxylate with Excess 4,4-Dimethoxybutylamine.

Trimethyl 1,2,4-benzenetricarboxylate (25.00 g, 0.0991 mol) was aminated with 42.62 g (0.320 mol) of 4,4-dimethoxybutylamine and 3.00 g (0.0102 mol) of dibutyl tin dimethoxide in 200 g of mixed xylenes according to the procedure used in Example 1. In this case, all but 25–30 g of the xylenes were removed via distillation. Upon cooling, ca. 50–70 g of hexane was added to the residual solution in order to induce the precipitation of a yellowish-white paste. The isolated precipitate amounted to 45.92 g. The infrared spectra (KBr) of this sample indicated the presence of both ester and amide moieties; 1735 (C=O, ester), 1635 (C=O, amide), 1560, 1310, 1130 cm$^{-1}$. NMR analysis revealed that ca. 75% of the ester groups were aminated with 4,4-dimethoxybutylamine. The product contained a mixture of both N, N', N''-tris(4,4-dimethoxybutyl)-1,2,4-benzenetricarboxamide and 4-[N-(4,4-dimethoxybutyl)aminocarbonyl]-N-(4,4-dimethoxybutyl)phthalimide. The following analyses are of the primary component, N, N', N''-tris(4,4-dimethoxybutyl)-1,2,4-benzenetricarboxamide; $^1$H NMR (CDCl$_3$; 300 MHz) δ1.50–1.80 (m, 12H, —CH$_2$CH$_2$CH—), 3.20–3.50 (m, 6H, —NH$_2$CH$_2$—), 3.28 (s, 18H, —OCH$_3$), 4.34 (m, 3H, CH$_2$CH —), 6.90–7.10 (br s, 3H, NH—CH$_2$—), 7.23–8.10 (m, 3H, ArH); MS (70 eV) m/z (rel. intensity) 75 (100.00), 84 (55.81), 258 (1.25), 276 (0.89), 290 (0.79), 324 (0.59), 394 (0.48), 508 (0.69), 540 (0.86); HRMS (FAB) 578.3054 (M+Na).

EXAMPLE 6

Amination of Trimethyl 1,2,4-Benzenetricarboxylate with Limited Amounts of 4,4-Dimethoxybutylamine-Preparation of 4-[N-(4,4-dimethoxybutyl)aminocarbonyl]-N-(4,4-dimethoxybutyl)phthalimide.

Trimethyl 1,2,4-benzenetricarboxylate (50.00 g, 0.1982 mol) was aminated with 55.94 g (0.4200 mol) of 4,4-dimethoxybutylamine and 10.00 g (0.0339 mol) of dibutyl tin dimethoxide in 500 g of mixed xylenes according to the procedure used in Example 1. In this case, a white precipitate was isolated upon cooling the reaction mixture. Recrystallization of the precipitate with mixed xylenes afforded 56.90 g of 4-[N-(4,4-dimethoxybutyl)aminocarbonyl]-N-(4,4-dimethoxybutyl)phthalimide, mp 101.5°-102° C.; IR (KBr) 1670 (C=O), 1655 (C=O), 1630, 1545, 1400, 1130, 1050, 965, 905, 740 cm$^{-1}$.

EXAMPLE 7

Preparation of N,N'-Bis(4,4-dimethoxybutyl)sebacamide.

Dimethyl sebacate (25.00 g, 0.1085 mol) was aminated with 30.63 g (0.230 mol) of 4,4-dimethoxybutylamine and 2.50 g (0.00847 mol) of dibutyl tin dimethoxide in 200 g of mixed xylenes according to the procedure used in Example 1. This procedure afforded 40.00 g (0.0925 mol, 85.2% isolated yield) of the desired N,N'-bis(4,4-dimethoxybutyl)sebacamide after recrystallization from mixed xylenes, mp 83.5°-85.5° C.; IR (KBr) 1640 (C=O), 1540, 1190, 1135, 1040 cm$^{-1}$; $^1$H NMR (CDCl$_3$; 300 MHz) δ1.13 (br s, 8H, —C$\underline{H}_2$—), 1.35-1.58 (m, 12H, —C$\underline{H}$2.00 (t, 4H, J=7.6 Hz, CO—C$\underline{H}_2$—), 3.08 (m, 4H, —NH$_2$C$\underline{H}_2$—), 3.16 (s 12H, —OC$\underline{H}_3$), 4.20 (t, 2H, J=5.1 Hz, C$\underline{H}_2$CH—), 6.38 (t, 2H, J=5.4 Hz, —N$\underline{H}$—CH$_2$—); $^{13}$C NMR (CDCl$_3$; 75.5 MHz) δ24.3, 25.5, 28.8, 28.9, 29.7, 36.3, 38.8, 52.7, 104.0, 173.0; MS (70 eV) m/z (rel. intensity) 353 (1.90), 305 (9.00), 236 (8.14), 128 (6.94), 100 (8.59), 85 (20.70) 84 (40.52), 75 (100.00); HRMS (FAB) 433.3278 (MH+).

EXAMPLE 8

Preparation of N,N'-Bis(4,4-dimethoxybutyl)adipamide.

Dimethyl adipate (25.00 g, 0.1435 mol) was aminated with 38.63 g (0.290 mol) of 4,4-dimethoxybutylamine and 2.50 g (0.00847 mol) of dibutyl tin dimethoxide in 200 g of mixed xylenes according to the procedure used in Example 1. This procedure afforded 36.47 g (0.0969 mol, 67.5% isolated yield) of the desired N,N'-bis(4,4-dimethoxybutyl)adipamide after recrystallization from mixed xylenes, mp 73°-75° C.; IR (KBr) 1640 (C=O), 1540, 1415, 1195, 1135, 1040 cm$^{-1}$; $^1$H NMR (CDCl$_3$; 300 MHz) δ8 1.42-1.63 (m, 12H, —C$\underline{H}_2$—), 2.06-2.18 (m, 4H, CO—C$\underline{H}_2$—), 3.13-3.20 (m, 4$\overline{H}$, —NH$_2$C$\underline{H}_2$—), 3.23 (s 12H, —OC$\underline{H}_3$), 4.27 (t, 2H, J=5.2 Hz, CH$_2$CH—), 6.38 (t, 2$\overline{H}$, J=5.5 Hz, —NH—CH$_2$—); $^{13}$C NMR (CDCl$_3$; 75.5 MHz) δ24.4, 25.0, 29.8, 36.0, 39.0, 52.8, 104.2, 172.7; MS (70 eV) m/z (rel. intensity) 286 (2.96), 244 (10.19), 228 (14.05), 212 (29.35), 85 (28.09), 84 (38.06), 75 (89.07), 70 (100.00); HRMS (FAB) 377.2652 (MH+).

EXAMPLE 9

Preparation of N,N'-Bis(4,4-dimethoxybutyl)cyclohexane-1,4-dicarboxamide.

A mixture of cis and trans-dimethyl cyclohexane-1,4-dicarboxylate (25.00 g, 0.125 mol) was aminated with 34.63 g (0.260 mol) of 4,4-dimethoxybutylamine and 2.50 g (0.00847 mol) of dibutyl tin dimethoxide in 200 g of mixed xylenes according to the procedure used in Example 1. This procedure afforded 10.94 g (0.0272 mol, 21.7% isolated yield) of the desired N,N'-bis(4,4-dimethoxybutyl)cyclohexane-1,4dicarboxamide after recrystallization from mixed xylenes, mp 191°-95° C.; IR (KBr) 1640 (C=O), 1545, 1260, 1135, 1050 cm$^{-1}$; $^1$H NMR (CDCl$_3$; 300 MHz) δ1.41-1.67, 1.75-1.90 (2m, 16H, —C$\underline{H}_2$—), 2.23 (br s, 2H, CO—C$\underline{H}$—), 3.13-3.20 (m, 4H, —NH$_2$C$\underline{H}_2$—), 3.23 (s, 12H, —OC$\underline{H}_3$), 4.27 (t, 2H, J=5.2 Hz, C$\underline{H}_2$CH—), 5.96 and 6.98 (2t, 2H, J=5.5 and 5.6 Hz, —N$\underline{H}$—CH$_2$—); $^3$C NMR (CDCl$_3$; 75.5 MHz) δ24.4, 26.5, 28.6, 29.8, 38.9, 41.7, 44.2, 52.8, 104.1, 174.7, 175.9; MS (70 eV) m/z (rel. intensity) 286 (2.96), 244 (10.19), 228 (14.05), 212 (29.35), 85 (28.09), 84 (38.06), 75 (89.07), 70 (100.00); HRMS (FAB) 403.2808 (MH+).

EXAMPLE 10

Amination of Triethyl Citrate with 4,4-Dimethoxybutylamine.

Triethyl citrate (25.00 g, 0.0905 mol) was aminated with 37.29 g (0.280 mol) of 4,4-dimethoxybutylamine and 2.50 g (0.00847 mol) of dibutyl tin dimethoxide in 200 g of mixed xylenes according to the procedure used in Example 1. After a 6 hr reaction time at 140° C., all volatile components were removed up to a boiling point of 100° C./1.0 mm Hg via vacuum distillation. The residual, viscous, red oil was analyzed by $^1$H and $^{13}$C NMR and found to have ca. 75% of the ester moieties converted to amides IR (KBr) 1740 (ester C=O), 1710 (ester C=O), 1650 (amide C=O), 1540, 1455, 1370, 1190, 1130, 1070, 910 cm$^{-1}$; $^1$H NMR (CDCl$_3$; 300 MHz) d 3.02 (s, —OC$\underline{H}_3$); $^{13}$NMR (CDCl$_3$; 75.5 MHz) δ169.5, 170.6, 173.3, 174.1 (amide and ester —CO—).

EXAMPLE 11

Preparation of N,N'-Bis(2,2-dimethoxyethyl)isophthalamide.

Dimethyl isophthalate (42.72 g, 0.220 mol) was aminated with 50.00 g (0.476 mol) of 2,2-dimethoxyethylamine and 10.00 g (0.0339 mol) of dibutyl tin dimethoxide in 250 g of mixed xylenes according to the procedure used in Example 1. After a 6 hr reaction time at 135° C., the procedure afforded 70.41 g (0.207 mol, 94.0 % isolated yield) of N,N'-bis(2,2-dimethoxyethyl)isophthalamide after recrystallization from mixed xylenes, mp 76.5°-78° C.; IR (KBr) 1670 (C=O), 1640 (C=O), 1550, 1525, 1295, 1280, 1130, 1115, 1065 cm$^{-1}$; MS (70 eV) m/z (rel. intensity)340 (M+) (0.07), 280 (1.06), 277 (1.03), 204 (2.24), 177 (1.22), 163 (1.06), 104 (5.87) 76 (8.12), 75 (100.00); HRMS (FAB) 341.1713 (MH+).

EXAMPLE 12

Preparation of N,N'-Bis(4,4-dimethoxybutyl)fumaramide from Dimethyl Maleate

Dimethyl maleate (100.00 g, 0.694 mol) was aminated with 173.15 g (1.30 mol) of 4,4-dimethoxybutylamine and 20.00 g (0.0678 mol) of dibutyl tin dimethoxide in 400 g of mixed xylenes according to the procedure used in Example 1. After a 6 hr reaction time at 135° C., the procedure afforded 62.48 g (0.1804 mol, 13.9% isolated yield) of N,N'-bis(4,4-dimethoxybutyl)maleamide after recrystallization from mixed xylenes, mp 170.5°–72° C.; IR (KBr) 1630 (C=O), 1555 (C=C), 1475, 1350, 1320, 1190, 1140, 1065 cm$^{-1}$; UV (CH$_3$OH) 1max (e) 218 nm (17100 1/M), 244 nm (11400 1/M); MS (70 eV) m/z (rel. intensity) 283 (2.61), 183 (3.51), 182 (2.65), 132 (5.36), 100 (21.10), 85 (17.63), 75 (100.00), 70 (49.52); HRMS (FAB) 347.2182

EXAMPLE 13

Preparation of N,N'-Bis(4,4-dimethoxybutyl)fumaramide from Dimethyl Fumarate Dimethyl fumarate (50.00 g, 0.347 mol) was aminated with 93.23 g (0.700 mol) of 4,4-dimethoxybutylamine and 10.00 g (0.0339 mol) of dibutyl tin dimethoxide in 200 g of mixed xylenes according to the procedure used in Example 1. After a 6 hr reaction time at 135° C., the procedure afforded 23.06 g (0.0666 mol, 19.2% isolated yield) of N,N'-bis(4,4-dimethoxybutyl)fumaramide after recrystallization from mixed xylenes, mp 172°–73° C.

EXAMPLE 14

Preparation of N,N'-Bis(4,4-dimethoxybutyl)malonamide

Dimethyl malonate (50.00 g, 0.378 mol) was aminated with 102.56 g (0.770 mol) of 4,4-dimethoxybutylamine and 10.00 g (0.0339 mol) of dibutyl tin dimethoxide in 200 g of mixed xylenes according to the procedure used in Example 1. After a 6 hr reaction time at 130° C., the procedure afforded 3.57 g (0.0107 mol, 2.82% isolated yield) of N,N'-bis(4,4-dimethoxybutyl)malonamide after recrystallization from mixed xylenes, mp 105° C. (dec.), IR (KBr) 1655 (C=O), 1545, 1470, 1380, 1135, 1070 cm$^{-1}$; MS (70 eV) m/z (rel. intensity) 255 (1.36), 239 (3.24), 180 (10.65), 128 (7.80), 85 (22.88), 84 (31.10), 75 (100.00), 70 (89.53); HRMS (FAB) 335.2182 (

EXAMPLE 15

Preparation of N,N'-Bis(4,4-dimethoxybutyl)terephthalamide Using Titanium Tetraisopropoxide as Catalyst.

Dimethyl terephthalate (25.00 g, 0.129 mol) was aminated with 37.29 g (0.280 mol) of 4,4-dimethoxybutylamine and 2.84 g (0.0100 mol) of titanium tetraisopropoxide in 200 g of mixed xylenes according to the procedure used in Example 1. A product mass of 7.49 g (0.0189 mol, 14.6% isolated yield) was realized after recrystallization with mixed xylenes; mp 129°–31° C.

EXAMPLE 16

Preparation of N,N'-Bis(4,4-dimethoxybutyl)terephthalamide Using Titanium Tetraisopropoxide as Catalyst.

Dimethyl terephthalate (25.00 g, 0.129 mol) was aminated with 37.29 g (0.280 mol) of 4,4-dimethoxybutylamine and 8.53 g (0.030 mol) of titanium tetraisopropoxide in 200 g of mixed xylenes according to the procedure used in Example 1. A product mass of 25.77 g (0.065 mol, 50.4% isolated yield) was realized after recrystallization with mixed xylenes; mp 129°–31° C.

EXAMPLE 17

Preparation of N,N'-Bis(4,4-dimethoxybutyl)terephthalamide Using Dibutyl Tin Oxide as Catalyst.

Dimethyl terephthalate (25.00 g, 0.129 mol) was aminated with 37.29 g (0.280 mol) of 4,4-dimethoxybutylamine and 4.98 g (0.020 mol) of dibutyl tin oxide in 200 g of mixed xylenes according to the procedure used in Example 1. A product mass of 44.14 g (0.111 mol, 86.3% isolated yield) was realized after recrystallization with mixed xylenes; mp 129°–31° C.

EXAMPLE 18

Preparation of N,N'-Bis(4,4-dimethoxybutyl)terephthalamide Using Dibutyl Tin Diacetate as Catalyst.

Dimethyl terephthalate (25.00 g, 0,129 mol) was aminated with 37.29 g (0.280 mol) of 4,4-dimethoxybutylamine and 7.34 g (0.021 mol) of dibutyl tin diacetate in 200 g of mixed xylenes according to the procedure used in Example 1. In this case; however, the reaction time was 17 hrs. A product mass of 34.57 g (0.0872 mol, 67.6% isolated yield) was realized after recrystallization with mixed xylenes; mp 129°–31° C.

EXAMPLE 19

Preparation of N,N'-Bis(4,4-dimethoxybutyl)terephthalamide Using Dibutyl Tin Dichloride as Catalyst.

Dimethyl terephthalate (25.00 g, 0,129 mol) was aminated with 37.29 g (0.280 mol) of 4,4-dimethoxybutylamine and 6.08 g (0,020 mol) of dibutyl tin dichloride in 200 g of mixed xylenes according to the procedure used in Example 1. In this case; however, the reaction time was 17 hrs. A product mass of 23.30 g (0.0588 mol, 45.6% isolated yield) was realized after recrystallization with mixed xylenes; mp 129°–31° C.

EXAMPLE 20

Preparation of N,N'-Bis(4,4-dimethoxybutyl)terephthalamide Using Dimethyl Tin Dichloride as Catalyst.

Dimethyl terephthalate (25.00 g, 0.129 mol) was aminated with 37.29 g (0.280 mol) of 4,4-dimethoxybutylamine and 4.39 g (0.020 mol) of dimethyl tin dichloride in 200 g of mixed xylenes according to the procedure used in Example 1. In this case; however, the reaction time was 17 hrs. A product mass of 23.60 g (0.0595 mol, 46.1% isolated yield) was realized after recrystallization with mixed xylenes; mp 129°–31° C.

TABLE 1
Example Structures

| Example No. | Catalyst | Product |
|---|---|---|
| 1 | (Bu)₂Sn(OCH₃)₂ | *(structure: 1,3-benzene dicarboxamide with two -NH-CH₂CH₂CH₂-CH(OCH₃)₂ groups)* |
| 2 | Ti(OiPr)₄ | |
| 3 | (Bu)₂Sn(OCH₃)₂ | *(structure: 1,4-benzene dicarboxamide with two -NH-CH₂CH₂CH₂-CH(OCH₃)₂ groups)* |
| 15 | Ti(OiPr)₄ | |
| 16 | Ti(OiPr)₄ | |
| 17 | (Bu)₂SnO | |
| 18 | (Bu)₂Sn(OAc)₂ | |
| 19 | (Bu)₂SnCl₂ | |
| 20 | (Me)₂SnCl₂ | |
| 4 | (Bu)₂Sn(OCH₃)₂ | *(structure: 1,3,5-benzene tricarboxamide with three -NH-CH₂CH₂CH₂-CH(OCH₃)₂ groups)* |
| 5 | (Bu)₂Sn(OCH₃)₂ | Mixture of *(structure with two amide groups and one aminomethyl group on benzene ring)* and *(phthalimide-type structure with amide and imide groups)* |
| 6 | (Bu)₂Sn(OCH₃)₂ | *(phthalimide-type structure with amide and imide groups bearing -CH₂CH₂CH₂-CH(OCH₃)₂ chains)* |

TABLE 1-continued

Example Structures

| Example No. | Catalyst | Product |
|---|---|---|
| 7 | (Bu)$_2$Sn(OCH$_3$)$_2$ | CH$_3$O-(CH$_2$)-NH-C(=O)-(CH$_2$)$_{10}$-C(=O)-NH-(CH$_2$)-CH(OCH$_3$)$_2$ (with CH$_3$O groups) |
| 8 | (Bu)$_2$Sn(OCH$_3$)$_2$ | CH$_3$O-(CH$_2$)-NH-C(=O)-(CH$_2$)$_4$-C(=O)-NH-(CH$_2$)-CH(OCH$_3$)$_2$ |
| 9 | (Bu)$_2$Sn(OCH$_3$)$_2$ | 1,4-cyclohexane-bis(C(=O)NH-CH$_2$CH$_2$CH$_2$CH(OCH$_3$)$_2$); mixture of cis and trans isomers |
| 10 | (Bu)$_2$Sn(OCH$_3$)$_2$ | tri-amide from citrate; mixture of partially and fully aminated triethyl citrate |
| 11 | (Bu)$_2$Sn(OCH$_3$)$_2$ | isophthaloyl-bis(NH-CH$_2$-CH(OCH$_3$)$_2$) |
| 12 | (Bu)$_2$Sn(OCH$_3$)$_2$ (from dimethyl maleate) | |
| 13 | (Bu)$_2$Sn(OCH$_3$)$_2$ (from dimethyl fumarate) | CH$_3$O-(CH$_2$)-NH-C(=O)-CH=CH-C(=O)-NH-(CH$_2$)-CH(OCH$_3$)$_2$ |
| 14 | (Bu)$_2$Sn(OCH$_3$)$_2$ | CH$_3$O-(CH$_2$)-NH-C(=O)-CH$_2$-C(=O)-NH-(CH$_2$)-CH(OCH$_3$)$_2$ |

EXAMPLE 21

Reaction of N,N'-Bis(4,4-dimethoxybutyl)isophthalamide with Pentaerythritol (Formation of a Thermoset Resin via Acetal Exchange)

A solution of 25.00 g (0.129 mol) of N,N'-bis(4,4-dimethoxybutyl)isophthalamide (prepared in Example 1), 8.76 g (0.064 mol) of pentaerythritol, and 0.609 g (0.0032 mol) of para-toluenesulfonic acid in 200 g of mixed xylenes was heated to 100° C. in a 500 mL flask fitted with a Dean-Stark trap with rapid stirring. After 20 min., approximately 5–6 mL of methanol was collected. Within an additional 20 min., the originally clear, colorless solution had yellowed and an amber precipitate began to form. The reaction mixture was maintained at 100° C. for an additional 2 hr. The resin was then isolated (12.88 g).

This example illustrates the reactivity of the acetal with multi-hydroxylated compounds and materials and demonstrates the utility of these multi-acetal compounds as cross-linking agents. This example also illustrates one set of conditions useful for promotion of acetal exchange (crosslinking). Another is the acid catalyzed cyclization and aminoplast formation when n=3 or 4 in structured formula (I) above.

EXAMPLE 22

Coatings Utility of ABAA Amides

High Solids Coatings

The control formulation used was an acid-cured polyester melamine system. Aroplaz 6755-A6-80 polyester was provided by Reichhold Chemicals, Inc. admixed as 13% by weight methoxy propanol acetate (Arcosolv PM acetate, CAS #108-65-6) and 7% by weight toluene (CAS #108-88-3). Cymel 303 from American Cyanamid was the source of hexamethoxymethylmelamine. paraToluenesulfonic acid catalyst was available as a 40% acid, 60% isopropanol solution sold as Cycat 4040 by American Cyanamid.

To prepare a nominal 70/30 resin/melamine curative coating 8.75 g Aroplaz 6755-A6-80 polyester resin was well mixed with 3.0 g Cymel 303. Sulfonic acid catalyst at 1% based on solids content, was then added and well mixed The coating formulation was spread onto a 4"×12"22 gauge unpolished cold-rolled steel test panel which had been wiped down with 1/1 methylethyl ketone/toluene to remove the last traces of oils. A Bird type film applicator with nickel-chrome finish was used to generate a 3" wide by 0.0015" thick wet film. The plate was allowed to stand 10 minutes in a fume hood, then placed in a vented, forced air convection oven at 350° F. for 20 minutes. For those films used to obtain dynamic mechanical data the preparation process was the same as above except for the addition of ~25 mg (1 drop) fluorinated alkylester flow modifier FC-430 from 3M to the formulation and treatment of the plates with Miller-Stephenson MS-136 fluorocarbon mold release to assist film removal.

Coatings Physical Property Data

Film hardness by pencil test was done following ASTM D 3363-74. Adhesion by tape test was measured according to ASTM D 3359-87, method B, with 1 mm grid spacing. Reverse impact data expressed in inch-pounds were generated using method ASTM D 2794-84. The indenter steel punch hemispheric head was ⅝ inch. Dynamic mechanical analyses were performed on a Rheometrics Solids Analyzer RSA II over -150° C. to 300° C. at 6.28 rad/sec using tension/compression rectangular tensile mode. Test strips of the films were ½" wide by 1" long.

Standard Polyester-Melamine Coatings

Coating 1 prepared from mixing 23.44 g Aroplaz 6755-A6-80 polyester resin with 8.04 g Cymel 303 hexamethoxymethylmelamine and 0.40 g Cycat 4040 para-toluenesulfonic acid catalyst was tested as noted above; tabulated data summarize critical parameters:

| Entry | Resin % | Melamine % | Curative % | Solids % | Catalyst % | 20 min. cure (°F.) | Thickness (mil) | Pencil Hardness | Scratch Adhesion | Reverse Impact |
|---|---|---|---|---|---|---|---|---|---|---|
| 1 | 70.0 | 30.0 | 0 | 85.1 | 0.60 | 350 | 1.0 | 2H | 0 | 40 |

It was noted that increased catalyst resulted in lower impact resistance. Lower cure temperatures improved physical properties at comparable catalyst levels. Using no catalyst at all was successful at the highest cure temperatures.

| Entry | Resin % | Melamine % | Curative % | Solids % | Catalyst % | 20 min. cure (°F.) | Thickness (mil) | Pencil Hardness | Scratch Adhesion | Reverse Impact |
|---|---|---|---|---|---|---|---|---|---|---|
| 2 | 70.0 | 30.0 | 0 | 85.1 | 1.0 | 350 | 1.0 | 4H | 0 | 30 |
| 3 | 70.0 | 30.0 | 0 | *75.2 | 1.0 | 350 | 1.1 | H | 0 | 4 |
| 4 | 70.0 | 30.0 | 0 | 75.2 | 1.0 | 300 | 1.2 | 4H | 0 | 140 |
| 5 | 70.0 | 30.0 | 0 | 75.2 | 0.5 | 300 | 1.1 | 2H | 1 | 220 |
| 6 | 70.0 | 30.0 | 0 | 85.1 | 0 | 350 | 1.1 | 4H | 5 | >350 |

*PM Acetate added to reduce viscosity; 1.3 g PM acetate added to 12 g batch.

The high degree of sensitivity of the formulation to catalyst and cure conditions may be due to melamine self-condensation.

Formaldehyde-free Curative Coatings

N,N'-Bis(4,4'-dimethoxybutyl)isophthalamide from Example 1 was dissolved in an equal weight of PM acetate at 60° C. A test resin formulation was made with half the melamine withdrawn and replaced by the bisphthalamide curative; 8.75 g Aroplaz 6755-A6-80 polyester, 1.50 g Cymel 303, 3.00 g bisphthalamide solution and 0.25 g Cycat 4040 were well mixed and a coating spread on plates with a 1.5 mil drawdown bar. Also made were coatings with 25% and 75% of the melamine withdrawn and replaced by an equal weight of bisisophthalamide:

| Entry | Resin % | Melamine % | Curative % | Solids % | Catalyst % | 20 min. cure (°F.) | Thickness (mil) | Pencil Hardness | Scratch Adhesion | Reverse Impact |
|---|---|---|---|---|---|---|---|---|---|---|
| 7 | 70.0 | 15.0 | 15.0 | 75.5 | 1.0 | 300 | 1.1 | 3H | 5 | 210 |
| 8 | 70.0 | 7.5 | 22.5 | 71.4 | 1.0 | 300 | 1.0 | H | 4 | <1 |
| 9 | 70.0 | 22.5 | 7.5 | 75.2 | 1.0 | 300 | 1.1 | 3H | 3 | 210 |

Replacement of hexafunctional melamine with difunctional formaldehyde-free bisisophthalamide led to improvement over the coating in entry 4 made using the same catalyst level and cure conditions. Replacement of hexamethoxymethylmelamine, which can generate formaldehyde, at either the 25 or 50 weight percent levels resulted in improved reverse impact and, unexpectedly, greatly improved scratch adhesion.

Similarly shown to improve coating performance was N,N'-bis(4,4'-dimethoxybutyl)tere-phthalimide from Example 3 when it was used as a curative:

| Curative | Midpoint Tg (°C.) | E' @ 130C (dynes/cm3) | Mc (g/g-mole) |
|---|---|---|---|
| none | 81 | $2.2 \cdot 10^8$ | 460 |
| isophthalamide | 71 | $9.4 \cdot 10^7$ | 1070 |
| terephthalamide | 75 | $9.9 \cdot 10^7$ | 1020 |
| sebacamide | 77 | $8.1 \cdot 10^7$ | 1240 |
| adipamide | 78 | $6.9 \cdot 10^7$ | 1460 |

The improved physical property performance for entries 7, 10, 13 and 16 upon formaldehyde-free curative

| Entry | Resin % | Melamine % | Curative % | Solids % | Catalyst % | 20 min. cure (°F.) | Thickness (mil) | Pencil Hardness | Scratch Adhesion | Reverse Impact |
|---|---|---|---|---|---|---|---|---|---|---|
| 10 | 70.0 | 15.0 | 15.0 | 75.5 | 1.0 | 300 | 1.2 | 2H | 5 | 200 |
| 11 | 70.0 | 7.5 | 22.5 | 71.4 | 1.0 | 300 | 1.1 | H | 5 | <1 |
| 12 | 70.0 | 22.5 | 7.5 | 75.2 | 1.0 | 300 | 1.1 | 4H | 0 | 50 |

The aliphatic diamides N,N'-bis(4,4-dimethoxybutyl)-sebacamide from example 7 (entries 13–15) and N,N'-bis(4,4-dimethoxybutyl)adipamide from example 8 (entries 16–18) were cured at 350° F. and were compared against the standards presented by entries 2 and 3, which also were made using 1% catalyst. Scratch adhesion was superior; reverse impact was again better up to equal weight displacement.

replacement of hexamethoxymethylmelamine may be in part attributed to reduced melamine self-crosslinking. That complex reaction chemistry is reviewed in Journal of Coatings Technology 64, no 804 69–77 (1992) by U. Samaraweera and F. N. Jones in the article 'Possible Reaction Pathways for Self-Condensation of Melamine Resins; Reversibility of Methylene Bridge Formation'. Bifunctional curatives used above are chain extenders

| Entry | Resin % | Melamine % | Curative % | Solids % | Catalyst % | 20 min. cure (°F.) | Thickness (mil) | Pencil Hardness | Scratch Adhesion | Reverse Impact |
|---|---|---|---|---|---|---|---|---|---|---|
| 13 | 70.0 | 15.0 | 15.0 | 75.5 | 1.0 | 350 | 1.0 | 3H | 5 | 145 |
| 14 | 70.0 | 7.5 | 22.5 | 71.4 | 1.0 | 350 | 1.0 | H | 5 | 2 |
| 15 | 70.0 | 22.5 | 7.5 | 80.0 | 1.0 | 350 | 1.2 | 3H | 5 | 50 |
| 16 | 70.0 | 15.0 | 15.0 | 75.5 | 1.0 | 350 | 1.0 | 3H | 5 | 165 |
| 17 | 70.0 | 7.5 | 22.5 | 71.4 | 1.0 | 350 | 0.9 | H | 4 | <1 |
| 18 | 70.0 | 22.5 | 7.5 | 80.0 | 1.0 | 350 | 1.2 | 3H | 4 | 55 |

A series of films were prepared using these above four bisamides at an equivalent molar replacement, that is, normalizing to the molecular weights of 396.5, 432.6 and 376.5 for the phthalamide, sebacamide and adipamide replacements of 390.5 m.w. hexamethoxymethylmelamine. Removal of 1.5 g melamine from a nominal ten g solids formulation therefore resulted in replacement by 1.52 g iso- or terephthalamide, 1.66 g sebacamide and 1.43 g adipamide. Removal of drawn films after curing for 20 minutes at 300° F. as described above allowed the following dynamic mechanical analysis of crosslinking as described in Journal of Coatings Technology, 46, no. 808, 29–42 (1992) by L. W. Hill in the article 'Structure/Property Relationships of Thermoset Coatings.

From the E' data at 130° C. the molecular weight between crosslinks (Mc) for these materials can be estimated by the equation $Mc = 3 \cdot \rho R \cdot T / E'$ where $\rho$ is the density, estimated as 1.0 g/cm$^3$, R is the gas constant (8.314·107g·cm$^2$/sec$^2$·g-mole·K) and T is the temperature in Kelvin. Mc is inversely proportional to the crosslink density. The midpoint Tg's, E' and Mc data are:

rather than crosslinkers, and will by their nature reduce crosslinking which might cause embrittlement, poor scratch adhesion and low impact resistance.

What is claimed is:

1. A crosslinking agent which is stable in both the solid state and in solution without undergoing uncontrolled self-crosslinking reactions represented by the structural formula:

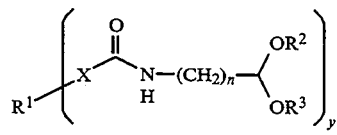

wherein R$^1$ is a C$_4$–C$_{10}$ aliphatic or aromatic multiradical; R$^2$ and R$^3$ are independently C$_1$–C$_6$ linear or branched alkyl, aryl or glycol, or R$^2$ and R$^3$ together form a C$_2$–C$_6$alkylene group; X is a single bond, an oxygen atom, or NH; n is from 1 to 4; and y is an integer from 2 to 5.

2. The crosslinking agent of claim 1 wherein n is 3 or 4.

* * * * *

UNITED STATES PATENT AND TRADEMARK OFFICE
CERTIFICATE OF CORRECTION

PATENT NO. : 5,336,807
DATED : August 9, 1994
INVENTOR(S) : William F. Burgoyne Jr., et al It is certified that error appears in the above-indentified patent and that said Letters Patent is hereby corrected as shown below:

Column 16, Line 54, insert the term --an-- in front of the term "aromatic".

Signed and Sealed this

Eleventh Day of October, 1994

Attest:

BRUCE LEHMAN

*Attesting Officer*      *Commissioner of Patents and Trademarks*